US011649465B2

(12) United States Patent
Li et al.

(10) Patent No.: US 11,649,465 B2
(45) Date of Patent: May 16, 2023

(54) METHODS AND COMPOSITIONS FOR INCREASING EXPRESSION OF GENES OF INTEREST IN A PLANT BY CO-EXPRESSION WITH P21

(71) Applicant: R.J. Reynolds Tobacco Company, Winston-Salem, NC (US)

(72) Inventors: Xingpeng Li, Lewisville, NC (US); Yijian He, Greensboro, NC (US); Emmett Ernest Hiatt, III, East Bend, NC (US); Darlene Madeline Lawson, Kernersville, NC (US)

(73) Assignee: R.J. Reynolds Tobacco Company, Winston-Salem, NC (US)

(*) Notice: Subject to any disclaimer, the term of this patent is extended or adjusted under 35 U.S.C. 154(b) by 211 days.

(21) Appl. No.: 16/127,818

(22) Filed: Sep. 11, 2018

(65) Prior Publication Data

US 2019/0093119 A1 Mar. 28, 2019

Related U.S. Application Data

(60) Provisional application No. 62/556,661, filed on Sep. 11, 2017.

(51) Int. Cl.

| | |
|---|---|
| ***C12N 15/82*** | (2006.01) |
| ***C07K 14/535*** | (2006.01) |
| ***C07K 16/18*** | (2006.01) |
| ***C12N 15/113*** | (2010.01) |

(52) U.S. Cl.

CPC ........ *C12N 15/8258* (2013.01); *C07K 14/535* (2013.01); *C07K 16/18* (2013.01); *C12N 15/113* (2013.01); *C12N 15/8205* (2013.01); *C12N 15/8209* (2013.01); *C12N 15/8216* (2013.01); *C12N 15/8243* (2013.01); *C12N 15/8257* (2013.01)

(58) Field of Classification Search

CPC .................................................. C12N 15/8258

See application file for complete search history.

(56) References Cited

U.S. PATENT DOCUMENTS 6,806,400 B1* 10/2004 Pruss .................. C07K 14/005 800/265
2010/0310604 A1* 12/2010 D'Aoust ........ C12Y 503/04001 800/298

FOREIGN PATENT DOCUMENTS

KR 2006 0107060 A 10/2006
WO WO 2012/098119 A2 7/2012

OTHER PUBLICATIONS

Ye et al (Structure, 2005, 13(9): 1375-1384).*
Chiba et al (Virology, 2006, 346: 7-14).*
Wang et al (Arch. Virol., 2016, 161: 1087-1090).*
Chapman et al (Genes & Development, 2004, 18: 1179-1186).*
GenBank KT203917 (published online Apr. 2016).*
Uniprot A0A0K1HRT6_9CLOS (published online Nov. 2015).*
Chiba et al. (Virology, 2006, 346: 7-14). (Year: 2006).*
Wang et al. (Arch. Virol, 2016, 161: 1087-1090). (Year: 2006).*
Chiba et al., Virology, 2006, vol. 346: pp. 7-14. (Year: 2006).*
Arzola, L., et al., "Transient Co-Expression of Post-Transcriptional Gene Silencing Suppressors for Increased in Planta Expression of a Recombinant Anthrax Receptor Fusion Protein," *International Journal of Molecular Sciences*, 2011, vol. 12(12), pp. 4975-4990.
Chapman, E., et al., "Viral RNA silencing suppressors inhibit the microRNA pathway at an intermediate step," *Genes & Development*, 2004, vol. 18(10), pp. 1179-11186.
Incarbone, M., et anon., "RNA silencing and its suppression: novel insights from in planta analyses," *Trends In Plant Science*, 2013, vol. 18(7), pp. 382-392.
Uniprot Database Accession No. A0A0K1HRT6, "Tobacco Virus 1," 2015, 1 page.
Wang, F., et al., "Complete genome sequence of tobacco virus 1, a closterovirus form *Nicotiana tabacum,* "*Arch Virol*, 2016, vol. 161(4), pp. 1087-1090.

* cited by examiner

*Primary Examiner* — Russell Kallis
(74) *Attorney, Agent, or Firm* — Womble Bond Dickinson (US) LLP

(57) ABSTRACT

Methods and compositions are provided for increasing the expression of a gene of interest in a plant by co-expressing the gene of interest with a p21 polynucleotide. The gene of interest can be endogenous or heterologous to the plant. Further provided are plants, such as tobacco plants, comprising a heterologous p21 polynucleotide. Co-expression of the p21 polynucleotide with a gene of interest in the plant increases the expression of the gene of interest when compared to a control plant. Accordingly, p21 co-expression can increase the expression of genes of interest encoding proteins such as defense proteins, enzymes, signaling proteins, reporter proteins, antibodies and fragments thereof, growth factors, cell surface receptor molecules, seed storage proteins, and fungicides in a plant.

17 Claims, 3 Drawing Sheets

Specification includes a Sequence Listing.

4 days post inoculation 3 days post inoculation

METHODS AND COMPOSITIONS FOR INCREASING EXPRESSION OF GENES OF INTEREST IN A PLANT BY CO-EXPRESSION WITH P21

CROSS-REFERENCE TO RELATED APPLICATIONS

This application claims the benefit of U.S. provisional application Ser. No. 62/556,661, filed Sep. 11, 2017, which is incorporated by reference herein in its entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of R60999 10490US SEQ LIST ST25.txt, a creation date of Sep. 11, 2018, and a size of 9118 Bytes. The sequence listing filed via EFS-Web is part of the specification and is hereby incorporated in its entirety by reference herein.

FIELD OF THE INVENTION

The present disclosure relates to methods and compositions for enhancing expression of genes of interest in plants. More particularly, the invention relates to such methods and compositions employing co-expression of a p21 polynucleotide with a gene of interest.

BACKGROUND

The use of recombinant proteins as medicaments and for industrial processes is increasing rapidly, and will continue to increase. Low production levels limit the commercial production of many valuable industrial and medicinal proteins. Foreign proteins can be vulnerable to the degradative action of both intracellular and extracellular proteases, and other production conditions. Correspondingly, the produced proteins are often harmful for the metabolism and growth of the host cell. A wide range of host cell systems have been developed in the past. An example is plant cells, which have the advantage of being considered safe and inexpensive.

Plant proteins and enzymes have long been exploited for many purposes, from viable food sources to biocatalytic reagents, or therapeutic agents. The development of transgenic and transfected plants and improvement in genetic analysis have brought renewed scientific significance and economic incentives to these applications. The concepts of molecular plant breeding and molecular plant farming, wherein a plant system is used as a bioreactor to produce recombinant bioactive materials, have received great attention. Accordingly, methods for increasing the expression of a gene of interest can create plants exhibiting commercially important phenotypic properties. Thus, it would be desirable to provide an improved method for increasing expression of a gene of interest in a plant.

SUMMARY OF THE DISCLOSURE

The present disclosure provides compositions and methods for increasing the expression of a gene of interest in a plant comprising co-expressing a p21 polynucleotide with the gene of interest. The p21 polynucleotide can have a nucleic acid sequence with at least 80% sequence identity to SEQ ID NO: 1 or an active fragment or variant thereof. In specific embodiments, the p21 polynucleotide comprises a polynucleotide having the nucleic acid sequence of SEQ ID NO: 1. Likewise, the heterologous p21 polynucleotide can encode a p21 polypeptide comprising an amino acid sequence with at least 80% identity to SEQ ID NO: 2. In specific embodiments, the heterologous p21 polynucleotide can encode a p21 polypeptide comprising SEQ ID NO: 2. In some embodiments, the fragments and variants of the p21 polynucleotide encode a polypeptide comprising a pfam11757 domain. Expression of the gene of interest can be increased by at least 10%, 20%, 30%, 40%, 50%, 60%, 70%, 80%, 90%, or 100% when compared to a control plant. The control plant can comprise the gene of interest but does not express a p21 polynucleotide.

In some embodiments, the gene of interest co-expressed with the p21 polynucleotide encodes a protein or peptide selected from the group consisting of defense proteins, enzymes, signaling proteins, reporter proteins, antibodies and fragments thereof, growth factors, cell surface receptor molecules, seed storage proteins, and fungicides. For example, the defense proteins can be antibodies, such as monoclonal antibodies. The enzymes can be an alpha-galactosidase or lysosomal acid lipase. The signaling protein can be a granulocyte colony-stimulating factor (G-CSF). The reporter protein can be a green fluorescent protein (GFP). In some embodiments, the gene of interest encodes a therapeutic protein. In particular embodiments, the gene of interest is endogenous to the plant or heterologous to the plant.

The p21 polynucleotide can be operably linked to a promoter active in the plant. In particular embodiments, the promoter is a constitutive promoter active in the plant. For example, the constitutive promoter can be a CaMV 35S promoter. In some embodiments, the p21 polynucleotide is operably linked to the gene of interest and/or a promoter active in the plant.

Introducing the p21 polynucleotide into the plant can be accomplished by transformation of the plant with an *Agrobacterium* tDNA vector comprising the p21 polynucleotide. In some embodiments, the p21 polynucleotide can be introduced into the plant with a vector, such as a viral vector, containing an expression construct comprising a p21 polynucleotide.

Plants used in the compositions and methods disclosed herein include crop plants, such as tobacco plants. The tobacco plant can be, for example, *Nicotiana tabacum*, *Nicotiana benthamiana*, or *Nicotiana rustica*. Thus, provided herein are transgenic plants comprising a heterologous p21 polynucleotide. The p21 polynucleotide can have a nucleic acid sequence with at least 80% sequence identity to SEQ ID NO: 1 or an active fragment or variant thereof. In specific embodiments, the p21 polynucleotide comprises a polynucleotide having the nucleic acid sequence of SEQ ID NO: 1. In some embodiments, the fragments and variants of the p21 polynucleotide encode a polypeptide comprising a pfam11757 domain. In addition to a heterologous p21 polynucleotide, the transgenic plant can also comprise at least one gene of interest encoding a protein or peptide selected from the group consisting of defense proteins, enzymes, signaling proteins, reporter proteins, antibodies and fragments thereof, growth factors, cell surface receptor molecules, seed storage proteins, and fungicides.

DETAILED DESCRIPTION OF THE PREFERRED EMBODIMENTS

Figure 1:
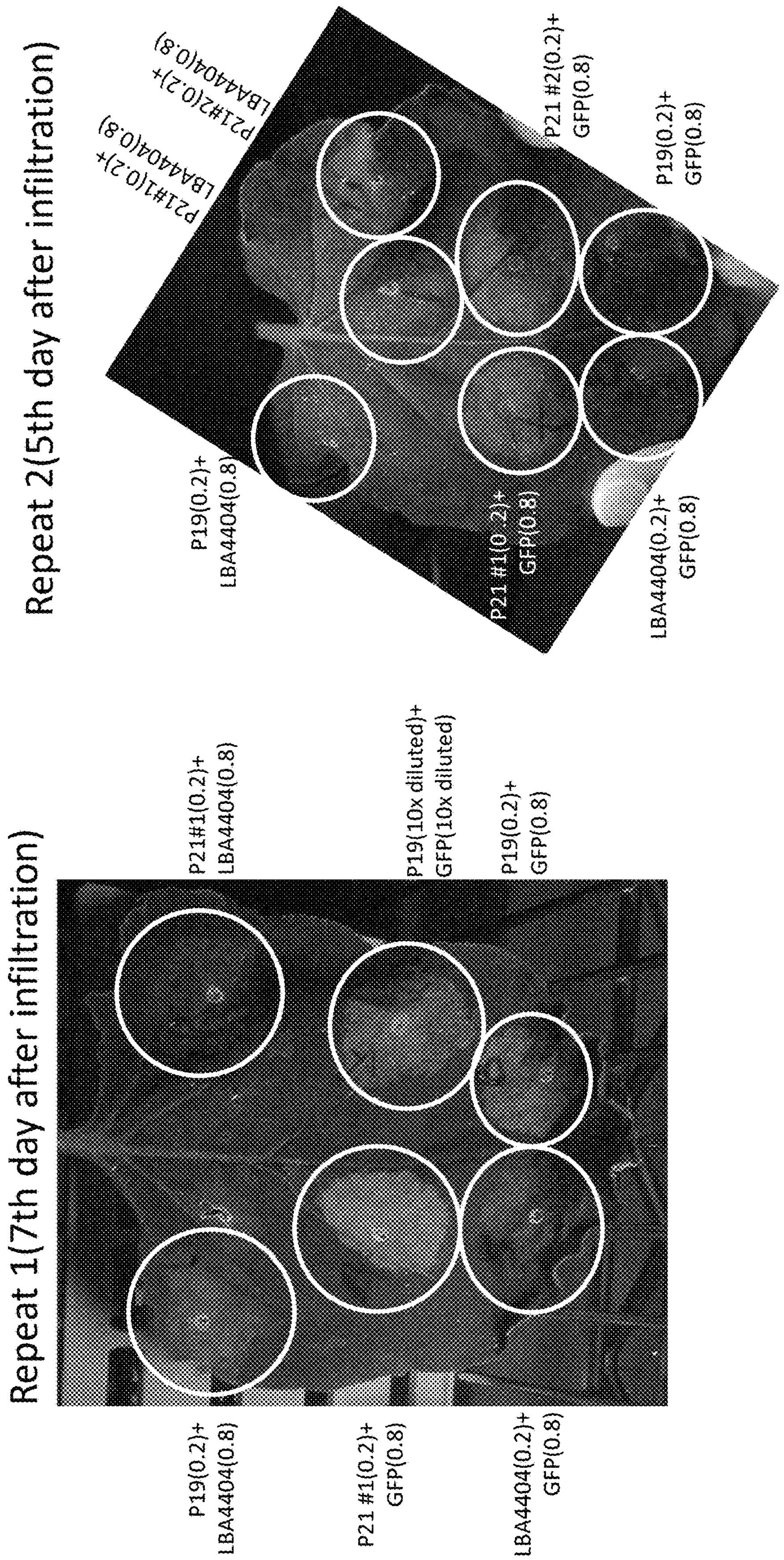
FIG. 1 shows the expression of green fluorescent protein (GFP) when co-expressed with P19, P21, or without co-expression. The numbers in the brackets are the $OD_{600}$ numbers representing the concentrations of *Agrobacterium*. Each infiltration treatment has the same total $OD_{600}$ number and total concentration. As evidenced by the figure, both p21 and p19 can enhance the expression of GFP. However, the expression of GFP was likely higher when co-expressed with p21 compared to the GFP expression level when co-expressed with p19.

The present disclosure now will be described more fully hereinafter. The disclosure may be embodied in many different forms and should not be construed as limited to the aspects set forth herein; rather, these aspects are provided so that this disclosure will satisfy applicable legal requirements. Like numbers refer to like elements throughout. As used in this specification and the claims, the singular forms “a,” “an,” and “the” include plural referents unless the context clearly dictates otherwise.

The disclosure provides compositions and methods for increasing the expression of a gene of interest in a plant or plant cell by co-expressing a p21 polynucleotide in the plant along with the gene of interest. As used herein a “p21” polynucleotide refers to a p21 polynucleotide isolated from a tobacco virus, such as the tobacco virus 1, a closteovirus from *Nicotiana tabacum*. In specific embodiments the p21 polynucleotide used in the methods and compositions disclosed herein comprises SEQ ID NO: 1, or a fragment or variant thereof. The complete nucleotide and amino acid sequence of the p21 polynucleotide and polypeptide is provided in Table 1, below. Co-expression of a gene of interest with the p21 polynucleotide can refer to overlapping temporal expression of the gene of interest and p21 polynucleotide. In some embodiments, co-expression refers to expression of the gene of interest and p21 polynucleotide such that the product of the p21 polynucleotide expression is present during expression of the gene of interest.

Accordingly, co-expressing a p21 polynucleotide in a plant along with a gene of interest can increase expression of the gene of interest when compared to a control plant. Thus, provided herein are methods for increasing expression of a gene of interest by introducing a p21 polynucleotide into a plant cell comprising a gene of interest. Likewise, plants comprising a heterologous p21 polynucleotide and a gene of interest are provided.

Co-expression of a p21 polynucleotide can increase the expression of any gene of interest in a plant. The expression of a gene of interest can be increased by about 10% to greater than about 90%, including greater than about 20%, about 30%, about 40%, about 50%, about 60%, about 70%, and about 80%. In specific embodiments, co-expressing a p21 polynucleotide increases the expression of a gene of interest by about 100%, 150%, 200%, 300%, 400%, 500%, or more when compared to expression of the gene of interest a control plant. Expression of p21 or a gene of interest can be measured by any means in the art for measuring gene expression. In some embodiments, expression can be measured by measuring the total amount of mRNA, protein, or any other product of gene expression. For example, gene expression can be measured by a nucleic acid analysis method such as PCR, or RT-PCR, or can be measured by a protein detection method, such as a Western blot analysis or any immunodetection method.

The gene of interest can be any gene capable of being expressed in a plant cell. In specific embodiments, the gene of interest encodes a protein or peptide including defense proteins, enzymes, signaling proteins, reporter proteins, antibodies and fragments thereof, growth factors, cell surface receptor molecules, seed storage proteins, and fungicides. For example, the gene of interest can encode proteins such as antibodies. The antibodies can be monoclonal antibodies, including therapeutic monoclonal antibodies. Therapeutic monoclonal antibodies include but are not limited to: abciximab (Reopro), adalimumab (Humira, Amjevita), ado-trastuzumab emtansine, alefacept (Amevive), alemtuzumab (Campath), basiliximab (Simulect), belimumab (Benlysta), bevacizumab (Avastin), bezlotoxumab (Zinplava), brentuximab vedotin (Adcetris), canakinumab (Ilaris), certolizumab pegol (Cimzia), cetuximab (Erbitux), daclizumab (Zenapax, Zinbryta), denosumab (Prolia, Xgeva), eculizumab (Soliris), efalizumab (Raptiva), gemtuzumab ozogamicin (Mylotarg), golimumab (Simponi, Simponi Aria), ibritumomab tiuxetan (Zevalin), inflectra (Remicade), ipilimumab (Yervoy), ixekizumab (Taltz), motavizumab (Numax), muronomab-CD3 (OKT3), natalizumab (Tysabri), nivolumab (Opdivo), obinutuzumab (Gazyva), olaratumab (Lartruvo), ofatumumab (Arzerra), omalizumab (Xolair), palivizumab (Synagis), panitumumab (Vectibix), pembrolizumab (Keytruda), pertuzumab (Perjeta), ranibizumab (Lucentis), raxibacumab (ABThrax), rituximab (Rituxan), tocilizumab (Actemra), tositumomab-I-131 (Bexxar), trastuzumab (Herceptin), ustekinumab (Stelara), secukinumab (Cosentyx), ustekinumab (Stelara).

The gene of interest can encode enzymes such as an alpha-galactosidase or lysosomal acid lipase. In particular embodiments, the gene of interest can encode a signaling protein including a granulocyte colony-stimulating factor (G-CSF). In some embodiments, the gene of interest encodes a reporter protein including a green fluorescent protein (GFP).

Examples of enzymes that may be produced from a gene of interest using the methods and compositions disclosed herein include, but are not limited to, glucanase, chymosin, proteases, polymerases, saccharidases, deyhdrogenases, nucleases, glucose oxidase, alpha-amylase, oxidoreductases (such as fungal peroxidases and laccases), xylanases, phytases, cellulases, hemicellulases, and lipases. This invention may also be used to produce enzymes such as, those used in detergents, rennin, horseradish peroxidase, amylases from other plants, soil remediation enzymes, and other such industrial proteins.

Examples of proteins that may be produced using the instant invention include, but are not limited to, blood proteins (e.g., serum albumin, Factor VII, Factor VIII (or modified Factor VIII), Factor IX, Factor X, tissue plasminogen factor, tissue plasminogen activator (t-PA), Protein C, von Willebrand factor, antithrombin III, and erythropoietin (EPO), urokinase, prourokinase, epoetin-alpha, colony stimulating factors (such as granulocyte colony-stimulating factor (G-CSF), macrophage colony-stimulating factor (M-CSF), and granulocyte macrophage colony-stimulating factor (GM-CSF)), cytokines (such as interleukins or interferons, interferon-beta-1a), integrins, addressins, selectins, homing receptors, surface membrane proteins (such as, surface membrane protein receptors), T cell receptor units, immunoglobulins, soluble major histocompatibility complex antigens, structural proteins (such as collagen, fibrin, elastin, tubulin, actin, and myosin), growth factor receptors, growth factors, growth hormone, cell cycle proteins, vaccines, fibrinogen, thrombin, cytokines, hyaluronic acid, and antibodies, such as therapeutic antibodies.

In some embodiments, the gene of interest encodes a therapeutic protein. Therapeutic proteins expressed according to the methods and compositions disclosed herein can be any protein that provides a beneficial effect to a subject, such as a human subject, upon administration of the protein. Generally, the therapeutic proteins of interest include, but are not limited to, hormones (insulin, thyroid hormone, catecholamines, gonadotrophines, trophic hormones, prolactin, oxytocin, dopamine, bovine somatotropin, porcine somatotropin, bovine chymosin, leptins and the like), growth hormones (e.g., human grown hormone), growth factors (e.g., epidermal growth factor, nerve growth factor, insulin-like growth factor (IGF-1), and the like), growth factor receptors, cytokines and immune system proteins (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interfersons, integrins, addressins, seletins, homing receptors, T cell receptors, immunoglobulins, soluble major histocompatibility complex antigens, immunologically active antigens such as bacterial, parasitic, or viral antigens or allergens), autoantigens, antibodies), envelope protein of the hepatitis B virus, enzymes (tissue plasminogen activator (TPA), streptokinase, cholesterol biosynthestic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases, alpha-L-iduronidase (rhIDU, laronidase), N-acetylgalactosamine-4-sulfatase (rhASB; galsulfase), dornase alpha, and the like), receptors (steroid hormone receptors, peptide receptors), binding proteins (steroid binding proteins, growth hormone or growth factor binding proteins and the like), transcription and translation factors, oncoprotiens or proto-oncoprotiens (e.g., cell cycle proteins), muscle proteins (myosin or tropomyosin and the like), myeloproteins, neuroactive proteins, tumor growth suppressing proteins (angiostatin or endostatin, both of which inhibit angiogenesis), anti-sepsis proteins (bactericidal permeability-increasing protein), structural proteins (such as collagen, fibroin, fibrinogen, elastin, tubulin, actin, and myosin), blood proteins (thrombin, serum albumin, Factor VII, Factor VIII (kogenate), insulin (BHI, humulin), follicle-stimulating hormone (FSH), Factor IX, Factor X, tissue plasminogen activator, Protein C, von Willebrand factor, antithrombin III, glucocerebrosidase, erythropoietin (EPO), granulocyte colony stimulating factor (GCSF) or modified Factor VIII, anticoagulants such as hirudin) and the like.

In specific embodiments, the methods and compositions disclosed herein may be utilized to produce vaccine components. In general, a vaccine component can be proteins, or portions of proteins, to which a human or animal immune system is exposed when the human or animal is infected with a pathogen, or suffering some other undesirable event (e.g., development of a tumor). Thus, proteins or polypeptides that may be formulated in a vaccine include, for example, viral coat proteins, viral G proteins, microbial cell wall proteins, microbial toxin proteins, tumor-specific antigens, etc.

The gene of interest can be endogenous to the plant or can be heterologous to the plant. As used herein, the term "heterologous" according to the present invention when used in reference to a nucleotide sequence is intended to mean a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" or "recombinant" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest. In specific embodiments, the p21 polynucleotide is heterologous to a plant comprising an endogenous gene of interest. In particular embodiments, the p21 polynucleotide is heterologous to a plant comprising a heterologous gene of interest.

The expression constructs (i.e., expression cassettes) disclosed herein can comprise a heterologous promoter operably linked to a p21 polynucleotide for expression in a plant. The term "operably linked" is intended to mean a functional linkage between two or more elements. For example, an operable linkage between a polynucleotide of interest (e.g., a p21 polynucleotide and/or a gene of interest) and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. In some embodiments, the p21 polynucleotide is operably linked to a promoter and the gene of interest.

A promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Furthermore, as used herein a chimeric gene comprises a coding sequence operably linked to a transcription initiation region that is heterologous to the coding sequence.

In some embodiments, the expression constructs provided herein can be combined with constitutive, tissue-preferred, developmentally-preferred or other promoters for expression of a p21 polynucleotide or a gene of interest in plants. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. A "tissue specific" promoter is a promoter that initiates transcription only in certain tissues. Unlike constitutive expression of genes, tissue-specific expression is the result of several interacting levels of gene regulation. As such, promoters from homologous or closely related plant species can be preferable to use to achieve efficient and reliable expression of transgenes in particular tissues. In some embodiments, the expression cassettes comprise a tissue-preferred promoter. A "tissue preferred" promoter is a promoter that initiates transcription mostly, but not necessarily entirely or solely in certain tissues. For example, nucleic acid molecules encoding a p21 polynucleotide or a gene of interest can be operably linked to leaf-preferred or stem-preferred promoters.

In some embodiments, the expression construct comprises a cell type specific promoter. A "cell type specific" promoter is a promoter that primarily drives expression in certain cell types in one or more organs, for example, vascular cells in roots, leaves, stalk cells, and stem cells. The expression construct can also include cell type preferred promoters. A "cell type preferred" promoter is a promoter that primarily drives expression mostly, but not necessarily entirely or solely in certain cell types in one or more organs, for example, vascular cells in roots, leaves, stalk cells, and stem cells. The expression constructs described herein can also comprise seed-preferred promoters. In some embodiments, the seed-preferred promoters have expression in embryo sac, early embryo, early endosperm, aleurone, and/or basal endosperm transfer cell layer (BETL). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures for each of these are incorporated herein by reference in their entirety.

Promoters that can drive gene expression in a plant seed-preferred manner with expression in the embryo sac, early embryo, early endosperm, aleurone and/or basal endosperm transfer cell layer (BETL) can be used in the compositions and methods disclosed herein. Such promoters include, but are not limited to, promoters that are naturally linked to *Zea mays* early endosperm 5 gene, *Zea mays* early endosperm 1 gene, *Zea mays* early endosperm 2 gene, GRMZM2G124663, GRMZM2G006585, GRMZM2G120008, GRMZM2G157806, GRMZM2G176390, GRMZM2G472234, GRMZM2G138727, *Zea mays* CLAVATA1, *Zea mays* MRP1, *Oryza sativa* PR602, *Oryza sativa* PR9a, *Zea mays* BET1, *Zea mays* BETL-2, *Zea mays* BETL-3, *Zea mays* BETL-4, *Zea mays* BETL-9, *Zea mays* BETL-10, *Zea mays* MEG1, *Zea mays* TCCR1, *Zea mays* ASP1, *Oryza sativa* ASP1, *Triticum durum* PR60, *Triticum durum* PR91, *Triticum durum* GL7, AT3G10590, AT4G18870, AT4G21080, AT5G23650, AT3G05860, AT5G42910, AT2G26320, AT3G03260, AT5G26630, AtIPT4, AtIPT8, AtLEC2, LFAH12. Additional such promoters are described in U.S. Pat. Nos. 7,803,990, 8,049,000, 7,745,697, 7,119,251, 7,964,770, 7,847,160, 7,700,836, U.S. Patent Application Publication Nos. 20100313301, 20090049571, 20090089897, 20100281569, 20100281570, 20120066795, 20040003427; PCT Publication Nos. WO/1999/050427, WO/2010/129999, WO/2009/094704, WO/2010/019996 and WO/2010/147825, each of which is herein incorporated by reference in its entirety for all purposes. Functional variants or functional fragments of the promoters described herein can also be operably linked to the nucleic acids disclosed herein.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci.* USA 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of an expression construct within a particular plant tissue. Tissue-preferred promoters are known in the art. See, for example, Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci.* USA 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci.* USA 90(20):9586-9590. In addition, the promoters of cab and rubisco can also be used. See, for example, Simpson et al. (1958) *EMBO J* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roIB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. The phaseolin gene (Mural et al. (1983) *Science* 23:476-482 and Sengopta-Gopalen et al. (1988) *PNAS* 82:3320-3324.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include, without limitation: picornavirus leaders, for example, EMCV leader (Encephalomyocarditis 5' noncoding region) (Elroy-Stein, et al., (1989) *Proc. Nat. Acad. Sci.* USA 86:6126-6130); potyvirus leaders, for example, TEV leader (Tobacco Etch Virus) (Allison, et al., (1986) *Virology* 154:9-20); MDMV leader (Maize Dwarf Mosaic Virus); human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) *Molecular Biology of RNA*, pages 237-256) and maize chlorotic mottle virus leader (MCMV) (Lommel, et al., (1991) *Virology* 81:382-385), herein incorporated by reference in their entirety. See, also, Della-Cioppa, et al., (1987) *Plant Physiology* 84:965-968, herein incorporated by reference in its entirety. Methods known to enhance mRNA stability can also be utilized, for example, introns, such as the maize Ubiquitin intron (Christensen and Quail, (1996) *Transgenic Res.* 5:213-218; Christensen, et al., (1992) *Plant Molecular Biology* 18:675-689) or the maize AdhI intron (Kyozuka, et al., (1991) *Mol. Gen. Genet.* 228:40-48; Kyozuka, et al., (1990) *Maydica* 35:353-357) and the like, herein incorporated by reference in their entirety.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, for example, transitions and transversions, may be involved.

Reporter genes or selectable marker genes may also be included in the expression cassettes of the present invention. Examples of suitable reporter genes known in the art can be found in, for example, Jefferson, et al., (1991) in Plant Molecular Biology Manual, ed. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain, et al., (1995) *Bio Techniques* 19:650-655 and Chiu, et al., (1996) *Current Biology* 6:325-330, herein incorporated by reference in their entirety.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella, et al., (1983) *EMBO J.* 2:987-992); kanamycin; neomycin; methotrexate (Herrera Estrella, et al., (1983) *Nature* 303:209-213; Meijer, et al., (1991) *Plant Mol. Biol.* 16:807-820); hygromycin (Waldron, et al., (1985) *Plant Mol. Biol.* 5:103-108 and Zhijian, et al., (1995) *Plant Science* 108:219-227); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-36); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518), herein incorporated by reference in their entirety.

Other polynucleotides that could be employed on the expression cassettes disclosed herein include, but are not limited to, examples such as GUS (beta-glucuronidase; Jefferson, (1987) *Plant Mol. Biol. Rep.* 5:387), GFP (green fluorescence protein; Chalfie, et al., (1994) *Science* 263:802), luciferase (Riggs, et al., (1987) *Nucleic Acids Res.* 15(19):8115 and Luehrsen, et al., (1992) *Methods Enzymol.* 216:397-414) and the maize genes encoding for anthocyanin production (Ludwig, et al., (1990) *Science* 247:449), herein incorporated by reference in their entirety.

In still other embodiments, the expression cassette can include an additional polynucleotide encoding an agronomically important trait, such as a plant hormone, plant defense protein, a nutrient transport protein, a biotic association protein, a desirable input trait, a desirable output trait, a stress resistance gene, a disease/pathogen resistance gene, male sterility gene, a developmental gene, a regulatory gene, a DNA repair gene, a transcriptional regulatory gene or any other polynucleotide and/or polypeptide of interest. In some embodiments, the expression cassette can include additional polynucleotides that downregulate the expression of genes responsible for agronomically important traits. For example, in some embodiments, the expression cassettes disclosed herein can comprise a nucleic acid sequence that downregulates expression of nicotine.

As used herein, "vector" refers to a DNA molecule such as a plasmid, cosmid, or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance. Provided herein are expression cassettes comprising nucleic acid molecules encoding a p21 polynucleotide located on a vector.

In specific embodiments, the p21 polynucleotide can be integrated into the genome of the plant. In some embodiments, the p21 polynucleotide can be provided in an expression cassette not integrated in the genome of the plant. For example, the expression cassette can be provided on a vector, such as a vector designed for *Agrobacterium* transformation comprising transfer DNA (tDNA) sequences. In some embodiments, the tDNA vector comprises two tDNA sequences flanking the p21 polynucleotide. In some embodiments, the expression cassette is provided on a viral vector, such as a tobacco virus 1 (TV1) vector, a tobacco mosaic virus (TMV) vector, or a tobacco rattle virus (TRV).

Some plant viruses have segmented genomes, in which two or more physically separate pieces of nucleic acid together make up the viral genome. In particular cases, these separate pieces are packaged together in the same viral capsid; in other viruses (i.e., those with multipartite genomes), each genome segment is packaged into its own viral particle. Infection of a plant by a viral genome can typically be accomplished by delivery either of plant viral nucleic acid (e.g., RNA) or capsid containing the packaged genome. In order to enter and infect a plant cell, plant viruses need to cross the cell wall, in addition to protective layers of waxes and pectins. Most or all plant viruses are thought to rely on mechanical breach of the cell wall, rather than on cell-wall-surface receptors, to enter a cell. Such a breach can be caused, for example, by physical damage to the cell, by an organism such as a bacterium, a fungus, a nematode, an insect, or a mite that can deliver the virus. In the laboratory, viruses are typically administered to plant cells simply by rubbing the virus on the plant.

Once the virus has entered (infected) a cell, it typically replicates within the infected cell and then spreads locally. For example, the virus can replicate and spread from cell to cell within leaves that were initially infected. Following local spread, the virus may move into uninfected leaves, e.g., upper leaves of the plant, which is referred to as systemic infection or systemic spread. In general, cell-to-cell spread of many plant viruses requires a functional movement protein while systemic spread requires a functional coat protein (and, generally, also a functional movement protein). In addition to functional movement and coat protein encoding components, viruses may contain additional components that are either required for local or systemic spread or facilitate such spread. These cis-acting components may be either coding or noncoding components. For example, they may correspond to portions of a 3' untranslated region (UTR, also referred to as NTR) of a viral transcript (i.e., they may provide a template for transcription of a 3' untranslated region of a viral transcript). Thus important viral components for infection can be either coding or noncoding regions of a viral genome.

In order to successfully establish either a local (intraleaf) or systemic infection a virus must be able to replicate. Many viruses contain genes encoding one or more proteins that participate in the replication process (referred to herein as replication proteins or replicase proteins). For example, many RNA plant viruses encode an RNA polymerase. Additional proteins may also be required (e.g., helicase or methyltransferase protein(s)). The viral genome may contain various sequence components in addition to functional genes encoding replication proteins, which are also required for or facilitate replication. Local intraleaf infections require the virus to move cell-to-cell as mediated by movement facilitating protein(s). For example in the case of TMV, the MP protein expression is required for intraleaf infections. The CP is not required. Other viruses, such as potatovirus potexvirus, require movement proteins and CP expression to move from cell-to-cell and establish an intraleaf infection.

In particular embodiments, viruses used in the methods and compositions disclosed herein are ssRNA viruses, and specifically, ssRNA viruses with a (+)-stranded genome. Techniques and reagents for manipulating the genetic material present in such viruses are well known in the art. Typically, for example, a DNA copy of the viral genome is prepared and cloned into an expression vector, particularly a bacterial vector or a Ti plasmid. Certain ssDNA viruses, including particularly geminiviruses, can also be used to deliver functional editing components to plant cells. It will be appreciated that in general the vectors and viral genomes of the invention may exist in RNA or DNA form. In addition, where reference is made to a feature such as a genome or portion thereof of an RNA virus, which is present within a DNA vector, it is to be understood that the feature is present as the DNA copy of the RNA form. This cDNA is converted into infectious RNA transcripts through transcription in vitro using T7 or other polymerase or in vivo using host DNA dependent RNA polymerase II using the *Agrobacterium* or particle delivered Ti DNA as template.

Viruses of a number of different types may be used in accordance with the methods and compositions disclosed herein for co-expression of a p21 polynucleotide and a gene of interest. Exemplary viruses include members of the Bromoviridae (e.g., bromoviruses, alfamoviruses, ilarviruses) and Tobamoviridae. Certain virus species include, for example, Alfalfa Mosaic Virus (A1MV), Apple Chlorotic Leaf Spot Virus, Apple Stem Grooving Virus, Barley Stripe Mosiac Virus, Barley Yellow Dwarf Virus, Beet Yellow Virus, Broad Bean Mottle Virus, Broad Bean Wilt Virus, Brome Mosaic Virus (BMV), Carnation Latent Virus, Carnation Mottle Virus, Carnation Ringspot Virus, Carrot Mottle Virus, Cassava Latent Virus (CL V), Cowpea Chlorotic Mottle Virus, Cowpea Mosaic Virus (CPMV), Cucumber Green Mottle Mosaic Virus, Cucumber Mosaic Virus, Lettuce Infectious Yellow Virus, Maize Chlorotic Mottle Virus, Maize Rayado Fino Virus, Maize Streak Virus (MSV), Parsnip Yellow Fleck Virus, Pea Enation Mosaic Virus, Potato Virus X, Potato Virus Y, Raspberry Bushy Dwarf Virus, Rice Necrosis Virus (RNV), Rice Stripe Virus, Rice Tungro Spherical Virus, Ryegrass Mosaic Virus, Soil-borne Wheat Mosaic Virus, Southern Bean Mosaic Virus, Tobacco Etch Virus (TEV), Tobacco Mosaic Virus (TMV), Tobacco Necrosis Virus, Tobacco Rattle Virus, Tobacco Ring Spot Virus, Tomato Bushy Stunt Virus, Tomato Golden Mosaic Virus (TGMV), and Turnip Yellow Mosaic Virus (TYMV). In specific embodiments the virus is a potyvirus, cucomovirus, bromovirus, tobravirus, or potexvirus.

Elements of these plant viruses can be genetically engineered according to known techniques (see, for example, (see, for example, Sambrook et al., Molecular Cloning, 2nd Edition, Cold Spring Harbor Press, NY, 1989; Clover et al., Molecular Cloning, IRL Press, Oxford, 1985; Dason et al., Virology, 172:285-292, 1989; Takamatsu et al., EMBO J6:307-311, 1987; French et al., Science 231: 1294-1297, 1986; Takamatsu et al., FEBS Lett. 269:73-76, 1990; Yusibov and Loesch-Fries, Virology, 208(1): 405-7, 1995. Spitsin et al., Proc Natl Acad Sci USA, 96(5): 2549-53, 1999, etc.) to generate viral vectors for use in accordance with the methods and compositions disclosed herein for co-expression of a p21 polynucleotide and a gene of interest.

In specific embodiments, the viral vectors used in the methods and compositions disclosed herein are TMV vectors modified to express a p21 polynucleotide and/or a gene of interest. As used herein a "TMV vector" is a DNA or RNA vector comprising at least one functional element of the TMV genome. TMV is a positive-sense single stranded RNA virus that infects a wide range of plants, especially tobacco and other members of the family Solanaceae. The TMV genome consists of a 6.3-6.5 kb single-stranded (ss) RNA. The 3'-terminus has a tRNA-like structure. The 5' terminus has a methylated nucleotide cap (m7G5'pppG). The genome can encode 4 open reading frames (ORFs), two of which produce a single protein due to ribosomal read-through of a leaky UAG stop codon. The 4 genes encode a replicase (with methyltransferase [MT] and RNA helicase [Hel] domains), an RNA-dependent RNA polymerase, a so-called movement protein (MP) and a capsid protein (CP).

As used herein an element of the TMV genome or TMV genome element refers to at least one nucleic acid molecule (i.e., gene) encoding a functional protein necessary for TMV replication and/or TMV infection. For example, an element of the TMV genome refers to a gene encoding a functional replicase or portion thereof (e.g., MT or Hel domain), a RNA-dependent RNA polymerase, movement protein, and/or capsid protein. In some embodiments, the modified TMV (mTMV) genome comprises genes encoding a replicase, movement protein, and capsid protein without a RNA-dependent RNA polymerase.

In particular embodiments of the methods and compositions disclosed herein, a TMV vector comprises all elements of the TMV genome. In other embodiments, the TMV genome elements are divided among at least two separate vectors, such that a complete and functional TMV can assemble following expression of the TMV elements from each of the vectors. Thus, when at least two vectors are employed, one or both of the vectors are incapable of systemic infection alone, but together can provide all functions needed to support systemic TMV infection and allow expression of functional editing components for modification of a target site of a plant genome. Thus the methods and compositions disclosed herein provide the recognition that viral components can complement each other in trans, to provide systemic infection capability and/or expression of functional editing components for modification of a target site in a plant genome. In specific embodiments, the TMV vector is based on the U1 strain of TMV. For example, the TMV vector can be a DN15 vector or a GENEWARE vector. The GENEWARE vector can be based on the pUC19 backbone. See, WO 99/36516, herein incorporated by reference.

In specific embodiments, the viral proteins involved in RNA replication are directly transcribed from the genomic RNA, whereas expression of internal genes occurs through the production of subgenomic RNAs. The production of subgenomic RNAs is controlled by RNA sequences in the TMV genome, which function as subgenomic promoters. The coat protein is translated from a subgenomic RNA and is the most abundant protein and RNA produced in the infected cell. In a TMV-infected plant there are several mg of coat protein produced per gram of infected tissue. Tobacco mosaic viral expression vectors take advantage of both the strength and duration of this strong subgenomic promoter's activity.

GENEWARE vectors allow expression of foreign proteins or peptides by two distinct methods: 1) Independent gene expression: by adding a foreign gene for expression in place of the virus coat protein so it will be expressed from the endogenous virus coat protein promoter. For example, the nucleic acid sequence encoding a p21 polynucleotide and/or gene of interest can be operably linked to the virus coat protein promoter. A second coat protein promoter of lesser transcriptional activity and non-identity in sequence is placed downstream of the heterologous coding region and a virus coat protein or selectable marker encoding gene may then be added. This encodes a third subgenomic RNA (including the MP expressing RNA) allowing the virus vector to express all requisite genes for virus replication and systemic movement in addition to the heterologous gene intended for overexpression. 2) Display of immunogenic peptides on the surface of virus particles: The TMV virion is a rigid rod of ~18 nm diameter and 300 nm length. The structure of the virion and coat protein has been determined by X-ray diffraction revealing a structure of approximately 2,130 coat protein subunits arranged in a right-handed helix encapsidating the genomic RNA, with 16.3 subunits per turn.

As used herein a p21 polynucleotide encompasses active fragments and variants of a p21 polynucleotide that maintain the ability to increase expression of a gene of interest. For example, in specific embodiments, the p21 polynucleotide is a fragment or variant of SEQ ID NO: 1. By "fragment" is intended a portion of the nucleotide sequence. Fragments of the disclosed nucleotide sequences may range from at least about 10, 16, 20, 50, 75, 100, 150, 200, 250, 300, 350, 400, 450 or 500 contiguous nucleotides, or up to the number of nucleotides present in a full-length p21 polynucleotide disclosed herein (for example, 10,948 nucleotides for SEQ ID NO: 1) so long as the fragment achieves the desired objective, i.e., increases the expression of a gene of interest upon co-expression.

By "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide comprises a naturally occurring nucleotide sequence, for example, a naturally occurring p21 polynucleotide. For polynucleotides, naturally occurring variants can be identified with the use of well-known molecular biology techniques such as, for example, polymerase chain reaction (PCR) and hybridization techniques as outlined elsewhere herein. Variant polynucleotides also include synthetically derived polynucleotides, such as those generated, for example, by using site-directed mutagenesis. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters commonly known in the art.

In particular embodiments, a p21 polynucleotide as disclosed herein may comprise the full-length nucleotide sequence of SEQ ID NO: 1 or a fragment of the nucleotide sequence of SEQ ID NO: 1. Additionally, p21 polynucleotides disclosed herein may comprise a variant of the full-length nucleotide sequence of SEQ ID NO: 1 or a variant of a fragment of the nucleotide sequence of SEQ ID NO: 1. Such variants will maintain at least 80% sequence identity to the nucleotide sequence of the native full-length sequence or fragment from which the variant is derived. In some embodiments, the heterologous p21 polynucleotide encodes a polypeptide comprising SEQ ID NO: 2, or an active fragment or variant thereof. For example, the p21 polynucleotide can encode any active p21 protein, such as a protein having at least 80%, 85%, 90%, 95%, 96%, 97%, 98%, 99%, or 100% sequence identity to the full length of SEQ ID NO: 2.

It is recognized that p21 polynucleotide mutants can be altered in various ways including amino acid substitutions, deletions, truncations, and insertions. Methods for such manipulations are generally known in the art. Nucleotide sequence variants and fragments of the p21 polynucleotide can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein.

In specific embodiments, fragments and variants of the p21 polynucleotide encode a protein having the conserved domain set forth in pfam11757. The pfam 11757 domain may identify a large family of putative suppressors of RNA silencing proteins, P20-P25, from ssRNA positive-strand viruses such as Closterovirus, Potyvirus and Cucumovirus families. RNA silencing is one of the major mechanisms of defense against viruses, and, in response, some viruses have evolved or acquired functions for suppression of RNA silencing. These counter-defensive viral proteins with RNA silencing suppressor (RSS) activity were originally discovered in the members of plant virus genera Potyvirus and Cucumovirus. Each of the conserved blocks of amino acids found in p21-like proteins corresponds to a computer-predicted alpha-helix, with the most C-terminal element being 42 residues long. This suggests conservation of the predominantly alpha-helical secondary structure in the p21-like proteins. In specific embodiments, active fragments and variants of a p21 polynucleotide can encode a polypeptide comprising a fragment or variant of the pfam11757 domain.

Thus, the expression cassettes disclosed herein can be based on the naturally occurring p21 polynucleotide sequences as well as variations and modified forms thereof. Such variants will continue to possess the desired activity. Where a functional polypeptide is to be expressed, the mutations that will be made in the DNA encoding the variant polypeptide must not place the sequence out of reading frame and optimally will not create complementary regions that could produce secondary mRNA structure. See, EP Patent Application Publication No. 75,444.

The deletions, insertions, and substitutions of the encoded polypeptides encompassed herein are not expected to produce radical changes in the characteristics of any active p21 RNA or protein. However, when it is difficult to predict the exact effect of the substitution, deletion, or insertion in advance of doing so, one skilled in the art will appreciate that the effect will be evaluated by routine screening assays. Deletions, insertions, and substitutions within a p21 polynucleotide are made such that the variant polynucleotide retains the desired activity, i.e., increases expression of a gene of interest upon co-expression.

Methods are provided for the co-expression of a p21 polynucleotide with a gene of interest in a plant by introducing a nucleic acid molecule comprising a p21 polynucleotide into the plant or plant cell. The terms "introducing" and "introduced" are intended to mean providing a nucleic acid (e.g., a recombinant expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid (e.g., p21 polynucleotide or expression construct) into a cell, means "transfection" or "transformation" or "transduction" and includes the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed.

"Stable transformation" is intended to mean that the nucleotide construct introduced into a host (i.e., a tobacco plant) integrates into the genome of the plant and is capable of being inherited by the progeny thereof. "Transient transformation" is intended to mean that a polynucleotide is introduced into the host (i.e., a plant) and expressed temporally.

Transformation protocols as well as protocols for introducing polynucleotide sequences into plants may vary depending on the type of plant or plant cell, i.e., monocot or dicot, targeted for transformation. Suitable methods of introducing polynucleotides into plant cells include microinjection (Crossway et al. (1986) *Biotechniques* 4:320-334), electroporation (Riggs et al. (1986) *Proc. Natl. Acad. Sci.* USA 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean);

McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci.* USA 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci.* USA 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the recombinant expression constructs disclosed herein can be provided to a tobacco plant using a variety of transient transformation methods. Such transient transformation methods include, but are not limited to, the introduction of the recombinant expression constructs directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotides can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, recombinant expression constructs disclosed herein may be introduced into tobacco plants by contacting the tobacco plants or plant parts with a virus or viral nucleic acids. Generally, such methods involve incorporating a nucleotide construct provided herein within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the genome of a tobacco plant or plant part. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the recombinant expression constructs comprising a p21 polynucleotide can be contained in a transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The recombinant expression construct is thereby integrated at a specific chromosomal position in the plant genome.

Any method can be used to introduce the nucleic acid molecules and expression cassettes disclosed herein into a plant or plant cell for expression of a p21 polynucleotide. For example, precise genome-editing technologies can be used to introduce the expression cassettes disclosed herein into the plant genome. In this manner, a nucleic acid sequence will be inserted proximal to a native plant sequence encoding the transporter protein of interest through the use of methods available in the art. Such methods include, but are not limited to, meganucleases designed against the plant genomic sequence of interest (D'Halluin et al 2013 Plant Biotechnol J 11: 933-941); CRISPR-Cas9, TALENs, and other technologies for precise editing of genomes (Feng, et al. Cell Research 23:1229-1232, 2013, Podevin, et al. *Trends Biotechnology* 31: 375-383, 2013, Wei et al. 2013 *J Gen Genomics* 40 : 281-289, Zhang et al 2013, WO 2013/026740); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. *Plant J* (2011) 701:147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65); Puchta, H. (2002) *Plant Mol Biol* 48:173-182).

The tobacco plant cells that have been transformed may be grown into plants in accordance with conventional methods. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic (i.e., gene of interest) identified. Two or more generations may be grown to ensure that expression of the desired phenotypic characteristic is stably maintained and inherited and then seeds harvested to ensure expression of the desired phenotypic characteristic has been achieved. In this manner, transformed seed (also referred to as "transgenic seed") having a recombinant expression construct disclosed herein, stably incorporated into their genome is provided.

Tobacco plant cells that have been transformed to have an expression construct provided herein can be grown into whole plants. The regeneration, development, and cultivation of plants from single plant protoplast transformants or from various transformed explants is well known in the art. See, for example, McCormick et al. (1986) *Plant Cell Reports* 5:81-84; Weissbach and Weissbach, In: Methods for Plant Molecular Biology, (Eds.), Academic Press, Inc. San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. Two or more generations may be grown to ensure that expression of the desired phenotypic characteristic is stably maintained and inherited and then seeds harvested to ensure expression of the desired phenotypic characteristic has been achieved. In this manner, the compositions presented herein provide transformed seed (also referred to as "transgenic seed") having a polynucleotide provided herein, for example, a recombinant miRNA expression construct, stably incorporated into their genome.

In specific embodiments, a nucleic acid molecule comprising a nucleotide sequence encoding p21 polynucleotide as described herein can be introduced into a *Nicotiana* plant, plant part, or plant cell. Subsequently, a *Nicotiana* plant or plant part having the introduced p21 polynucleotide sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to increase the expression of a gene of interest. Plant forming conditions are well known in the art and discussed briefly elsewhere herein.

Plants, plant cells, plant parts, and seeds, and grain comprising a p21 polynucleotide and a gene of interest as described elsewhere herein are provided. In specific embodiments, the plants and/or plant parts comprise stably incorporated in the genome at least one expression cassette comprising a p21 polynucleotide operably linked to a promoter and a heterologous gene of interest. As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The expression cassettes disclosed herein may be used for transformation of any plant species, including, but not limited to, monocots and dicots. In specific embodiments, the plant is a tobacco plant. For example, any tobacco species can be modified according to the methods disclosed herein to express a p21 polynucleotide. "Tobacco" or "tobacco plant" refers to any species in the *Nicotiana* genus that produces nicotinic alkaloids. In certain embodiments, tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Pasado, Cubano, Jatim and Bezuki tobaccos), light air cured (e.g., North Wisconsin and Galpao tobaccos), Indian air cured, Red Russian and Rustica tobaccos, as well as various other rare or specialty tobaccos and various blends of any of the foregoing tobaccos. Descriptions of various types of tobaccos, growing practices and harvesting practices are set forth in Tobacco Production, Chemistry and Technology, Davis et al. (Eds.) (1999), which is incorporated herein by reference. Various representative other types of plants from the *Nicotiana* species are set forth in Goodspeed, The Genus *Nicotiana*, (Chonica Botanica) (1954); U.S. Pat. No. 4,660,577 to Sensabaugh, Jr. et al.; U.S. Pat. No. 5,387,416 to White et al. and U.S. Pat. No. 7,025,066 to Lawson et al.; US Patent Appl. Pub. Nos. 2006/0037623 to Lawrence, Jr. and 2008/0245377 to Marshall et al.; each of which is incorporated herein by reference. Exemplary *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia*, and *N. spegazzinii.*

*Nicotiana* species can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO 2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference. Most preferably, the tobacco materials are those that have been appropriately cured and aged. Especially preferred techniques and conditions for curing flue-cured tobacco are set forth in Nestor et al., Beitrage Tabakforsch. Int., 20 (2003) 467-475 and U.S. Pat. No. 6,895,974 to Peele, which are incorporated herein by reference. Representative techniques and conditions for air curing tobacco are set forth in deRoton, C. et al. Beitrage Tabakforsch. Int., 2005, 21, 6, 305-320 and Staaf, M. et al. Beitrage Tabakforsch. Int. 2005, 21, 6, 321-330, which are incorporated herein by reference. Certain types of unusual or rare tobaccos can be sun cured. Manners and methods for improving the smoking quality of Oriental tobaccos are set forth in U.S. Pat. No. 7,025,066 to Lawson et al., which is incorporated herein by reference. Representative Oriental tobaccos include katerini, prelip, komotini, xanthi and yambol tobaccos. Tobacco compositions including dark air cured tobacco are set forth in US Patent Appl. Pub. No. 2008/0245377 to Marshall et al., which is incorporated herein by reference. See also, types of tobacco as set forth, for example, in US Patent Appl. Pub. No. 2011/0247640 to Beeson et al., which is incorporated herein by reference. Co-expression of a p21 polynucleotide along with a gene of interest from tobacco plants can increase the expressing of the gene of interest when compared to a control plant.

Further examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and Eucalyptus. In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments soybean plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

As used herein the term plant includes whole plants, plant parts, such as plant organs (e. g. leaves, stems, roots, etc.), seeds, differentiated or undifferentiated plant cells, and progeny of the same. Plant material includes without limitation seeds, suspension cultures, embryos, meristematic regions, callus tissues, leaves, roots, shoots, stems, fruit, gametophytes, sporophytes, pollen, and microspores.

A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which does not express the p21 polynucleotide described herein); (c) a plant or plant cell which is a non-transformed segregant among progeny of a subject plant or plant cell; or (d) the subject plant or plant cell itself, under conditions in which a heterologous p21 polynucleotide is not expressed. In some embodiments, a control level of expression can be the level of expression detected only at a minimal or background level similar to other genes that are not expressed in the plant.

The modified tobacco plants disclosed herein co-expressing a p21 polynucleotide and a gene of interest can be harvested and processed into a tobacco product. As used herein a tobacco product includes leaf tobacco, shredded tobacco, cut tobacco, ground tobacco, powder tobacco, tobacco extract, nicotine extract, smokeless tobacco, moist or dry snuff, kretek, pipe tobacco, cigar tobacco, cigarillo tobacco, cigarette tobacco, chewing tobacco, bidis, bits, cigarette, cigarillo, a non-ventilated recess filter cigarette, a vented recess filter cigarette, a cigar, and tobacco-containing gum, lozenges, patches, electronic cigarettes, or any combination thereof.

TABLE 1

| p21 nucleic acid sequence |
|---|
| p21 nucleic acid sequence (SEQ ID NO: 1) |
| ATGAAGTTGTATATCCAAGTCAAGTTCTACGAAAGCTACTTGAAACTAA |
| TCACTGACTTGTTGGAAGCGATAAACGCATCCAACTCATCTAACGAAAA |
| ACTAGTAGAGTGGGTGACAGACTTCACCGATCTGTGTTCCCGCTTGCAG |
| GCTTTAAAAAGCGACGTAAATGACGCTAAACGCGAAGAAAGCGCGAACA |
| ACTTGACCAGGAAGGCGAACATACTAAAACTAGCTGGAGACAACCTCGC |
| TTCCATACGGGATGAGTTGCGAAAGAGAGTGTTTCGCGATATTATCGAT |
| CTGAGCACAGAAGACACCCTTAGGTTTTTTGTTGCGAGGTTCATGGAAG |
| TGACTTCACATACAAAGGACGAGTCTCTTTCGTACAACGTGCGCGACAT |
| CGTAAACACAGTTCTGAGGAGAATATCGTCGGAACGTAGCCTAGATGTG |
| TCGACGAACACGTTCAAACAGTGCGATTTGCTACGCATGCAGAAATCCC |
| TACGAAGTGTGTGGAAACACACTCTAGGGCACAGCGAAGCTGAGCTATT |
| TGTGGAAGAAAAATAG |
| p21 amino acid sequence (SEQ ID NO: 2) |
| MKLYIQVKFYESYLKLITDLLEAINASNSSNEKLVEWVTDFTDLCSRLQ |
| ALKSDVNDAKREESANNLTRKANILKLAGDNLASIRDELRKRVFRDIID |
| LSTEDTLRFFVARFMEVTSHTKDESLSYNVRDIVNTVLRRISSERSLDV |
| STNTFKQCDLLRMQKSLRSVWKHTLGHSEAELFVEEK |

TABLE 1-continued

| p21 nucleic acid sequence |
|---|
| **p19 nucleic acid sequence (SEQ ID NO: 3)** |
| ATGGAACGAGCTATACAAGGAAACGACGCTAGGGAACAAGCTAACAGTG |
| AACGTTGGGATGGAGGATCAGGAGGTACCACTTCTCCCTTCAAACTTCC |
| TGACGAAAGTCCGAGTTGGACTGAGTGGCGGCTACATAACGATGAGACG |
| AATTCGAATCAAGATAATCCCCTTGGTTTCAAGGAAAGCTGGGGTTTCG |
| GGAAAGTTGTATTTAAGAGATATCTCAGATACGACAGGACGGAAGCTTC |
| ACTGCACAGAGTCCTTGGATCTTGGACGGGAGATTCGGTTAACTATGCA |
| GCATCTCGATTTTTCGGTTTCGACCAGATCGGATGTACCTATAGTATTC |
| GGTTTCGAGGAGTTAGTATCACCGTTTCTGGAGGGTCGCGAACTCTTCA |
| GCATCTCTGTGAGATGGCAATTCGGTCTAAGCAAGAACTGCTACAGCTT |
| GCCCCAATCGAAGTGGAAAGTAATGTATCAAGAGGATGCCCTGAAGGTA |
| CTGAGACCTTCGAAAAAGAAAGCGAGTAA |
| **p19 amino acid sequence (SEQ ID NO: 4)** |
| MERAIQGNDAREQANSERWDGGSGGTTSPFKLPDESPSWTEWRLHNDET |
| NSNQDNPLGFKESWGFGKVVFKRYLRYDRTEASLHRVLGSWTGDSVNYA |
| ASRFFGFDQIGCTYSIRFRGVSITVSGGSRTLQHLCEMAIRSKQELLQL |
| APIEVESNVSRGCPEGTETFEKESE |

The following examples are provided to illustrate further aspects associated with the present disclosure, but should not be construed as limiting the scope thereof. Unless otherwise noted, all parts and percentages are by dry weight.

EXPERIMENTAL

Example 1

Transformation of *Agrobacterium* by Electroporation

The p21 nucleotide sequence (SEQ ID NO: 1) was artificially synthesized and cloned into expression vector pRI-101_AN vector's MCS (Multiple Cloning Site) region before transformation. The transformation of *Agrobacterium* is performed according to the user manual of *Agrobacterium tumefaciens* LBA4404 Electro-Cells (Takara Bio Inc). In summary, the procedure included thawing tubes of *Agrobacterium tumefaciens* LBA4404 Electro-Cells on ice. About 1 ng of vector plasmid DNA expressing a p21 polynucleotide or p19 polynucleotide was added to 20 μl of competent cells on ice in a 1.5 ml tube, and mixed gently with the pipette. The mixture was transferred to an ice-chilled 0.1 cm electroporation cuvette (Sigma-Aldrich Lot #3110) and electroporated using BTX ECM630 Electro Cell Manipulator with the setting: 25 μF, 200Ω and 2 kV.

The cuvette was taken out, and 1 ml of SOC medium was added and transferred to a 15 ml Falcon tube. The mixture was incubated for 1 hour at 30° C., shaking at 100 rpm. 100 μl of cells were plated on LB agar plates with 50 μg/ml kanamycin and 50 μg/ml streptomycin, followed by incubation for up to 3 days at 28° C.

Example 2

Infiltration of *Agrobacterium* Cells into *N. benthamiana*

*Agrobacterium* cells were infiltrated into a host *N. benthamiana* plant as follows:

A single *Agrobacterium* colony was inoculated into 5 ml LB with appropriate antibiotics (e.g., 50 μg/ml kanamycin, 50 μg/ml streptomycin and 25 μg/ml Rifampin) and grown at 30° C., overnight. 1 ml culture was removed and added to 25 ml LB with appropriate antibiotics and grown at 30° C., overnight.

The culture was centrifuged at 3000 rpm for 10 minutes at room temperature. The resulting cell pellet of culture was resuspended in 1 ml infiltration buffer [10 mM MES (pH 5.6), 10 mM MgSO4 and 150 μM Acetosyringone]. The suspension was centrifuged at 3000 rpm for 10 minutes at room temperature and the cell pellet of culture was resuspended in 1.5 ml infiltration buffer. The suspensions were shaken gently for 2~3 hours at room temperature.

Agrobacteria suspensions were mixed together to the desired final $OD_{600}$ values and co-infiltrated into the leaves of *N. benthamiana* with a 1 mL needleless syringe. *Agrobacterium* carrying EGFP vector was diluted to a final OD600=0.8. P19 or TV-P21 were diluted to a final $OD_{600}$=0.2. *Agrobacterium* LBA4404 was used to bring each co-infiltration mixture to a total $OD_{600}$=1.0 to make all mixtures have the same cell density. At 5~7 days post infiltration, the expression of EGFP in *N. benthamiana* leaves was measured with UV-light. As shown in FIG. 1, both p21 and p19 can enhance the expression of GFP. However, the expression of GFP was likely higher when co-expressed with p21 compared to the GFP expression level when co-expressed with p19.

Example 3 p21 Expression

Viral expression vectors must solve several problems for efficient heterologous gene expression. The measurement of protein expression in whole plants is a function of virus replication, mRNA encoding heterologous gene sequences expression by vectors, translation of these mRNAs, genetic stability of the virus genome containing the full heterologous gene element, expression of relevant local and systemic movement proteins, evading host RNA silencing and other immune responses. The relative size and placement of the heterologous gene elements impact expression (reviewed in Pogue et al., 2002 and Hefferon BioMed Research International, Volume 2014 (2014), Article ID 785382, 6 pages). The larger the heterologous gene insertion, the less "fit" the vector is found, and less gene expression is observed. This is generally a result of slower virus RNA multiplication but also genetic instability of the virus genome and loss of heterologous gene sequences. The forces that impact the genetic stability of heterologous sequences in the RNA virus genomes are the efficiency of virus RNA movement locally and systemically as well as evading RNA inhibitory immune responses the plant host mounts in response to the dsRNAs produced during virus replication. RDR6, DCL4 and HEN1 are factors required for initiation or maintenance of virus induced gene silencing in growing tissues. DCL4 produces 21 nt viral siRNAs, which are amplified by RDR6 (Blevins et al., 2006; Dunoyer et al., 2005). The amplified 21 nt siRNAs then target viral RNA for silencing and restrict virus infection. Other viral gene silencing suppressor, such as potyvirus HC-Pro, tombusvirus P19 and closterovirus p21, bind siRNAs and prevent protein microRNA methylation by HEN1 (Blevins et al., 2006; Lakatos et al., 2004, 2006; Merai et al., 2006; Yu et al., 2006). This inhibition of RNAi activities has been linked to the ability of poorly optimized TMV-based vectors to create efficient expression systems. Co-expression of p21 and other silencing suppressors enables intron-less TMV vectors to be successfully transmitted from the plant nucleus after Agro-infiltration and produced enhanced levels of heterologous proteins (See, U.S. Pat. Nos. 8,936,937, 8,871,997, 6,632,980, 6,395,962, 5,939,541, and Pogue, G. P., et al. (2002) Ann. Rev. Phytopathol. 40:45-74).

Large genetic insertions such as full monoclonal antibodies (Mabs) and antibody fragments (FAbs) in TMV-based vectors is greatly facilitated by transgenic over-expression of the TMV movement protein 30K (Reinl, US Patent application publication 2004/0110930). The 30K protein is not a significant silencing suppressor gene, but has been shown to dramatically enhance virus cell-to-cell movement. Further, expression of silencing suppressor HC-Pro has been shown to enhance virus vector expression. This facilitation is expected to be seen by co-expression of the silencing suppressor p21.

Transgenic *Nicotiana benthamiana* plants are engineered to express p21 through the described CaMV 35S promoter—p21—nos terminator construct generated by *Agrobacterium*-mediated transformation. Plants over-expressing p21 are infected with TMV-GFP vectors as well as PXV-GFP and TRV-GFP vectors to produce enhanced GFP fluorescence. Expression of Fab fragments by TMV vectors is enhanced in *Nicotiana benthamiana* plants expressing p21 compared with wild type *Nicotiana benthamiana* plants. Finally, mAb expression using TMV vectors expressing antibody heavy chain and PVX vectors expressing antibody light chains by dual vector Agro-infiltration is enhanced in *Nicotiana benthamiana* plants expressing p21 compared with wild type *Nicotiana benthamiana* plants.

Example 4

Quantification of Overexpression

Construction of TV-P21 and P19 Expression Vectors

Two expression vectors, TV1-P21_pRI_101-An and P19-pRI_101-An, were generated to test if co-expression with P21 can increase expression level of Green Fluorescence Protein (GFP) gene and to compare P21 with P19. The synthetic DNA of P21 (SEQ ID NO: 1) or P19 gene (SEQ ID NO: 3) was digested with restriction enzyme NdeI and BamHI and cloned into NdeI-BamHI digested pRI_101-An expression vector (Takara Catalog #: 3262) to generate TV1-P21_pRI_101-An or P19-pRI_101-An vector.

The expression vector pEGAD (Arabidopsis Biological Resource Center Stock #: CD3-389, Ref. 1) was used to express GFP gene with either the P21 or the P19 gene.

Transformation of *Agrobacterium* by Electroporation

The transformation of *Agrobacterium* was performed according to the user manual of *Agrobacterium tumefaciens* LBA4404 Electro-Cells (Takara Catalog #: 18313015). The procedure includes:

1. Tubes of *Agrobacterium tumefaciens* LBA4404 Electro-Cells were thawed on ice.
2. 1 ng of plasmid DNA of TV1-P21_pRI_101-An, P19-pRI_101-An or pEGAD was added to 20 μl of competent cells on ice in a 1.5 ml tube, and mixed gently with the pipette.
3. The mixture was transferred to an ice chilled 0.1 cm electroporation cuvette (Sigma-Aldrich Catalog #: Z706078-50EA) and performed electroporation using BTX ECM 630 Electroporation System (Harvard Apparatus Catalog #: MA1 45-0051) with the setting: 25 μF, 200Ω, and 2 kV.
4. The cuvette was removed and 1 ml of SOC medium (Takara Bio Catalog #: 18313015) was added the mixture was transferred to a 15 ml Falcon tube.
5. The mixture was incubated for 1 hour at 30° C., shaking at 100 rpm.
6. After incubation, the mixture was plated with 100 μl of cells on LB agar plates with 50 μg/ml kanamycin and 50 μg/ml streptomycin and incubated for up to 3 days at 28° C.

Infiltration of *Agrobacterium* Cells into *Nicotiana benthamiana* Plant

Figure 2:
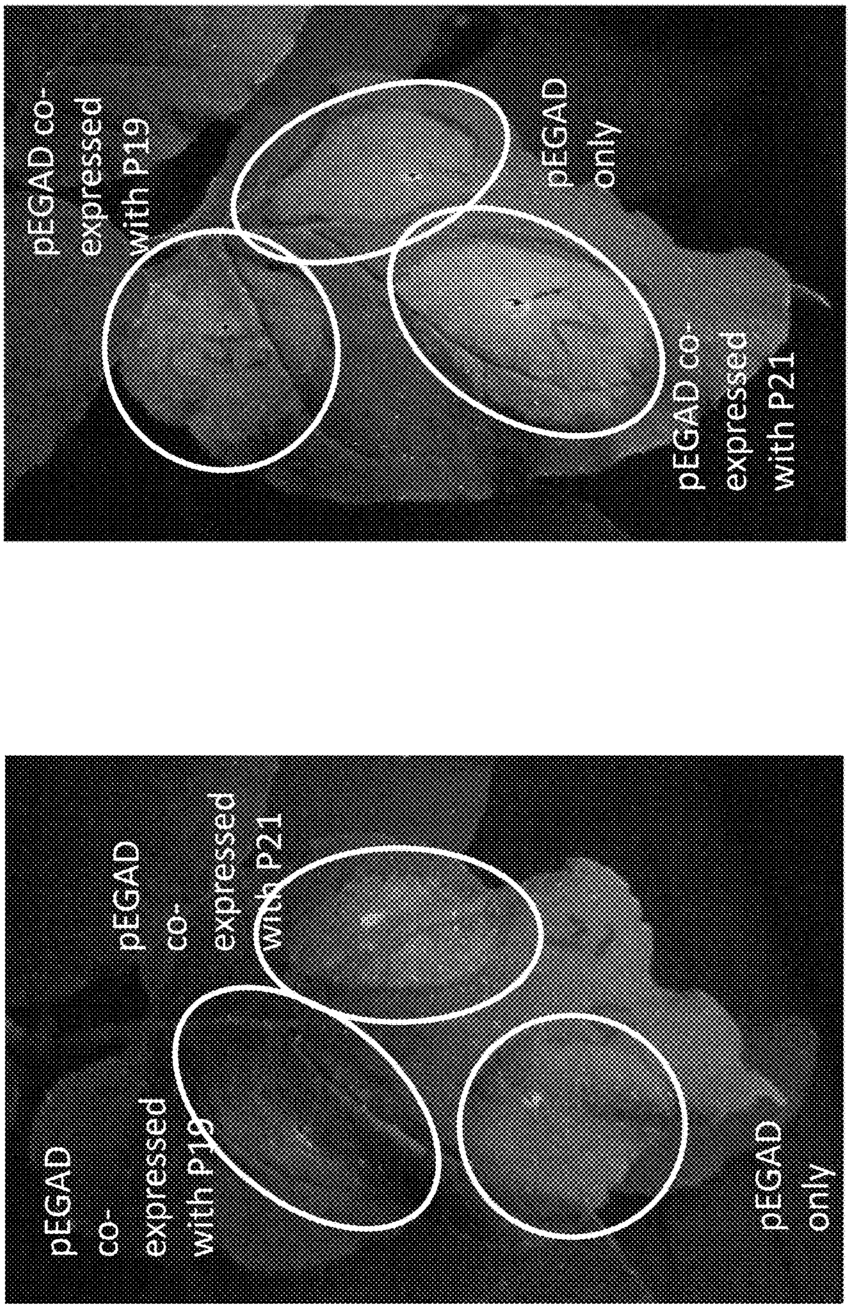
FIG. 2 shows the expression levels of GFP gene in *Nicotiana benthamiana* leaves were checked under UV-light following infiltration with GFP construct.
Figure 3:
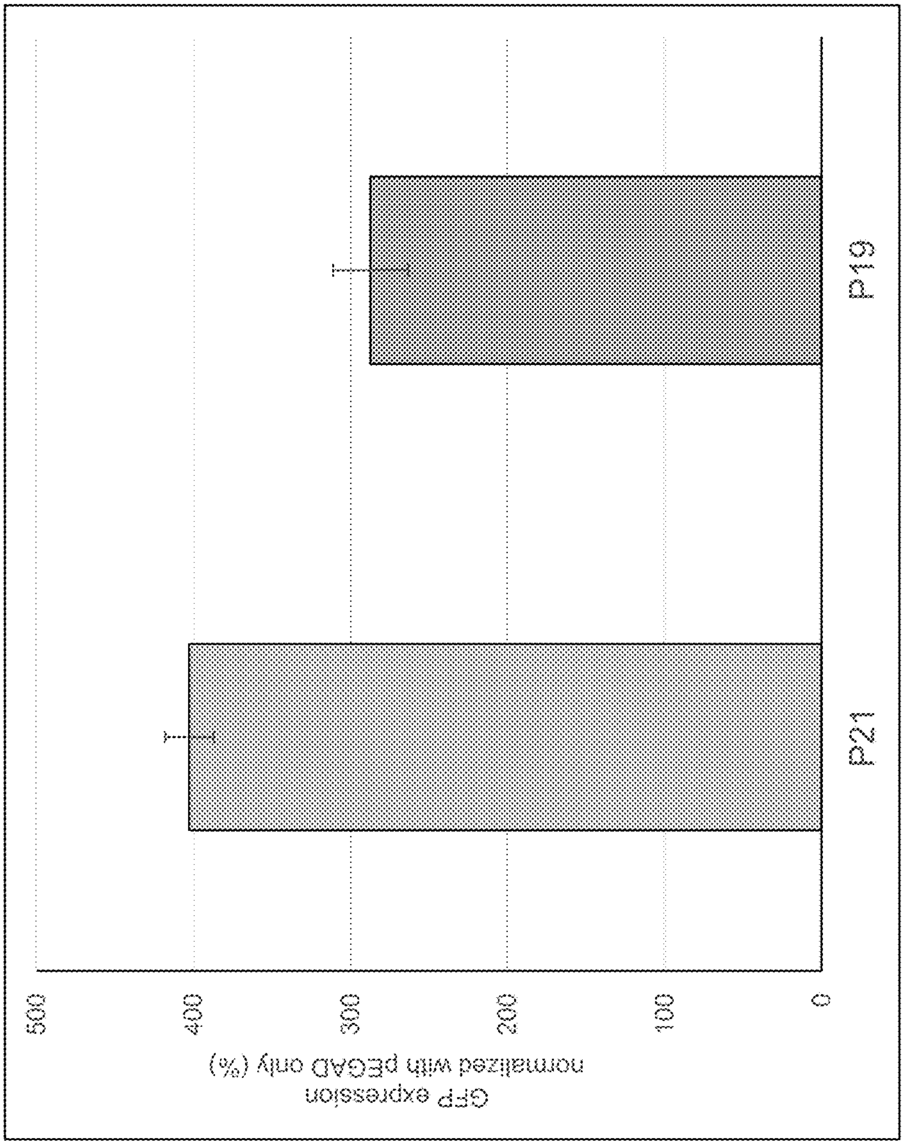
FIG. 3 shows The GFP protein expression levels were compared using a GFP ELISA kit. The expressions when co-expression with P21 and P19 were normalized against the GFP expression without co-expression. This figure showed the result of three technical replications. Error bars represent standard deviation.

*Agrobacterium* cells were infiltrated into host *Nicotiana benthamiana* plant as follows:

1. Incubated single *Agrobacterium* colony into 5 ml LB medium with appropriate antibiotics (e.g., 50 μg/ml kanamycin, 50 μg/ml streptomycin and 25 μg/ml Rifampin).
2. Grow at 30° C., overnight.
3. Took out 1 ml culture and added to 25 ml LB with appropriate antibiotics.
4. Grow at 30° C., overnight.
5. Centrifuged the culture at 3000 rpm for 10 minutes at room temperature.
6. Suspended the cell pellet of culture in 1 ml infiltration buffer [10 mM MES (pH 5.6), 10 mM $MgSO_4$ and 150 μM Acetosyringone].
7. Centrifuged the suspension at 3000 rpm for 10 minutes at room temperature.
8. Suspended the cell pellet of culture in 1.5 ml infiltration buffer. Shake the suspensions gently for 2~3 hours at room temperature.
9. Agarobacteria suspensions were mixed together to the desired final $OD_{600}$ values and were co-infiltrated into the leaves of *Nicotiana benthamiana* with a 1 mL needleless syringe. *Agrobacterium* carrying pEGAD vector was diluted to a final $OD_{600}$=0.8. *Agrobacterium* carrying TV1-P21_pRI_101-An or P19-pRI_101-An was diluted to a final $OD_{600}$=0.2. *Agrobacterium* LBA4404 was used to bring each co-infiltration mixture to a total $OD_{600}$=1.0 to make all mixtures have the same cell density.
10. At 3 and 4 days post infiltration, the expression levels of GFP gene in *Nicotiana benthamiana* leaves were checked under UV-light. The results (FIG. 2) showed that the expression level of GFP gene was higher when co-expressed with P21 compared to the GFP gene expression level when co-expressed with P19.

Quantification of GFP Protein Expression Using Enzyme-Linked Immunosorbent Assay (ELISA)

The expression levels of GFP protein were quantified with GFP ELISA Kit (Cell Biolabs Catalog #: AKR-121) as follows:

1. At 3 days post infiltration, the inoculated *Nicotiana benthamiana* leaf discs were collected with liquid nitrogen using a 0.5-cm diameter leaf puncher. The tissues were frozen at −80° C. until ready for use.
2. The frozen tissues were homogenized with 0.05 M pH 7.0 Sodium phosphate buffer (ref. 2) containing cOmplete Mini Protease Inhibitor Cocktail (Sigma-Aldrich Catalog #: 11836153001) (150 μL buffer for 4 leaf discs).
3. The Lysates were allowed to incubate on ice for 10 min and then centrifuged at 4° C., 10000×g for 5 minutes. The supernatants were transferred to new tubes and kept on ice. The total protein concentrations were measured using a Pierce 660 nm Protein Assay Kit (Thermofisher Catalog #: 22660).

11. GFP protein was quantified in the protein extracts using a GFP ELISA kit (Cell Biolabs Catalog #: AKR-121) following the manufacture's instruction. The result of ELISA assay (FIG. 4) demonstrated that the GFP protein expression was higher when co-expressed with P21 compared to the GFP protein expression level when co-expressed with P19.

That which is claimed:

1. A method of increasing expression of a gene of interest in a plant, plant part, or plant cell, the method comprising introducing a heterologous p21 polynucleotide into a genome of the plant, plant part, or plant cell, wherein the heterologous p21 polynucleotide encodes a polypeptide comprising an amino acid sequence with at least 90% sequence identity to SEQ ID NO: 2, and wherein expression of a co-expressed gene of interest is increased by at least 300% when compared to expression of the gene of interest in a control plant, plant part, or plant cell that does not express a p21 polynucleotide.

2. The method of claim 1, wherein the heterologous p21 polynucleotide encodes a polypeptide comprising an amino acid sequence with at least 95% sequence identity to SEQ ID NO: 2.

3. The method of claim 1, wherein the heterologous p21 polynucleotide encodes a polypeptide comprising an amino acid sequence of SEQ ID NO: 2.

4. The method of claim 1, wherein the heterologous p21 polynucleotide comprises a nucleic acid sequence with at least 95% sequence identity to SEQ ID NO: 1.

5. The method of claim 1, wherein the heterologous p21 polynucleotide comprises the nucleic acid sequence of SEQ ID NO: 1.

6. The method of claim 1, further comprising introducing the gene of interest into the plant, plant part, or plant cell.

7. The method of claim 1, wherein the gene of interest is endogenous to the plant, plant part, or plant cell.

8. The method of claim 1, wherein the gene of interest is heterologous to the plant, plant part, or plant cell.

9. The method of claim 1, wherein the gene of interest encodes a therapeutic protein.

10. The method of claim 1, wherein the gene of interest encodes a protein or peptide selected from the group consisting of defense proteins, enzymes, signaling proteins, reporter proteins, antibodies, growth factors, cell surface receptor molecules, seed storage proteins, and fungicides.

11. The method of claim 1, wherein the heterologous p21 polynucleotide is operably linked to the gene of interest.

12. The method of claim 1, wherein introducing the heterologous p21 polynucleotide into the plant, plant part, or plant cell comprises transforming the plant, plant part, or plant cell with an *Agrobacterium* T-DNA vector comprising an expression construct comprising the heterologous p21 polynucleotide.

13. The method of claim 1, wherein introducing the heterologous p21 polynucleotide into the plant, plant part, or plant cell comprises inoculating the plant, plant part, or plant cell with a viral vector containing an expression construct comprising the heterologous p21 polynucleotide.

14. The method of claim 1, wherein the plant, plant part, or plant cell is a crop plant, plant part, or plant cell.

15. The method of claim 1, wherein the plant, plant part, or plant cell is a tobacco plant, plant part, or plant cell.

16. The method of claim 15, wherein the tobacco plant, plant part, or plant cell is *Nicotiana tabacum, Nicotiana benthamiana*, or *Nicotiana rustica.*

17. A transgenic plant, plant part, or plant cell comprising a heterologous p21 polynucleotide, wherein the heterologous p21 polynucleotide encodes a polypeptide comprising an amino acid sequence with at least 90% sequence identity to SEQ ID NO: 2.

* * * * *

```
                    SEQUENCE LISTING


<160> NUMBER OF SEQ ID NOS: 4

<210> SEQ ID NO 1
<211> LENGTH: 555
<212> TYPE: DNA
<213> ORGANISM: Tobacco mosaic virus
<220> FEATURE:
<221> NAME/KEY: CDS
<222> LOCATION: (1)..(555)

<400> SEQUENCE: 1

atg aag ttg tat atc caa gtc aag ttc tac gaa agc tac ttg aaa cta       48
Met Lys Leu Tyr Ile Gln Val Lys Phe Tyr Glu Ser Tyr Leu Lys Leu
1               5                   10                  15

atc act gac ttg ttg gaa gcg ata aac gca tcc aac tca tct aac gaa       96
Ile Thr Asp Leu Leu Glu Ala Ile Asn Ala Ser Asn Ser Ser Asn Glu
            20                  25                  30

aaa cta gta gag tgg gtg aca gac ttc acc gat ctg tgt tcc cgc ttg      144
Lys Leu Val Glu Trp Val Thr Asp Phe Thr Asp Leu Cys Ser Arg Leu
        35                  40                  45

cag gct tta aaa agc gac gta aat gac gct aaa cgc gaa gaa agc gcg      192
Gln Ala Leu Lys Ser Asp Val Asn Asp Ala Lys Arg Glu Glu Ser Ala
    50                  55                  60

aac aac ttg acc agg aag gcg aac ata cta aaa cta gct gga gac aac      240
Asn Asn Leu Thr Arg Lys Ala Asn Ile Leu Lys Leu Ala Gly Asp Asn
65                  70                  75                  80

ctc gct tcc ata cgg gat gag ttg cga aag aga gtg ttt cgc gat att      288
Leu Ala Ser Ile Arg Asp Glu Leu Arg Lys Arg Val Phe Arg Asp Ile
                85                  90                  95

atc gat ctg agc aca gaa gac acc ctt agg ttt ttt gtt gcg agg ttc      336
Ile Asp Leu Ser Thr Glu Asp Thr Leu Arg Phe Phe Val Ala Arg Phe
            100                 105                 110

atg gaa gtg act tca cat aca aag gac gag tct ctt tcg tac aac gtg      384
Met Glu Val Thr Ser His Thr Lys Asp Glu Ser Leu Ser Tyr Asn Val
        115                 120                 125

cgc gac atc gta aac aca gtt ctg agg aga ata tcg tcg gaa cgt agc      432
Arg Asp Ile Val Asn Thr Val Leu Arg Arg Ile Ser Ser Glu Arg Ser
    130                 135                 140

cta gat gtg tcg acg aac acg ttc aaa cag tgc gat ttg cta cgc atg      480
Leu Asp Val Ser Thr Asn Thr Phe Lys Gln Cys Asp Leu Leu Arg Met
145                 150                 155                 160

cag aaa tcc cta cga agt gtg tgg aaa cac act cta ggg cac agc gaa      528
Gln Lys Ser Leu Arg Ser Val Trp Lys His Thr Leu Gly His Ser Glu
                165                 170                 175

gct gag cta ttt gtg gaa gaa aaa tag                                  555
Ala Glu Leu Phe Val Glu Glu Lys
            180


<210> SEQ ID NO 2
<211> LENGTH: 184
```

```
<212> TYPE: PRT
<213> ORGANISM: Tobacco mosaic virus 1

<400> SEQUENCE: 2

Met Lys Leu Tyr Ile Gln Val Lys Phe Tyr Glu Ser Tyr Leu Lys Leu
1               5                   10                  15

Ile Thr Asp Leu Leu Glu Ala Ile Asn Ala Ser Asn Ser Ser Asn Glu
            20                  25                  30

Lys Leu Val Glu Trp Val Thr Asp Phe Thr Asp Leu Cys Ser Arg Leu
        35                  40                  45

Gln Ala Leu Lys Ser Asp Val Asn Asp Ala Lys Arg Glu Glu Ser Ala
    50                  55                  60

Asn Asn Leu Thr Arg Lys Ala Asn Ile Leu Lys Leu Ala Gly Asp Asn
65                  70                  75                  80

Leu Ala Ser Ile Arg Asp Glu Leu Arg Lys Arg Val Phe Arg Asp Ile
                85                  90                  95

Ile Asp Leu Ser Thr Glu Asp Thr Leu Arg Phe Phe Val Ala Arg Phe
            100                 105                 110

Met Glu Val Thr Ser His Thr Lys Asp Glu Ser Leu Ser Tyr Asn Val
        115                 120                 125

Arg Asp Ile Val Asn Thr Val Leu Arg Arg Ile Ser Ser Glu Arg Ser
    130                 135                 140

Leu Asp Val Ser Thr Asn Thr Phe Lys Gln Cys Asp Leu Leu Arg Met
145                 150                 155                 160

Gln Lys Ser Leu Arg Ser Val Trp Lys His Thr Leu Gly His Ser Glu
                165                 170                 175

Ala Glu Leu Phe Val Glu Glu Lys
            180


<210> SEQ ID NO 3
<211> LENGTH: 519
<212> TYPE: DNA
<213> ORGANISM: Tomato bushy stunt virus
<220> FEATURE:
<221> NAME/KEY: CDS
<222> LOCATION: (1)..(519)

<400> SEQUENCE: 3

atg gaa cga gct ata caa gga aac gac gct agg gaa caa gct aac agt       48
Met Glu Arg Ala Ile Gln Gly Asn Asp Ala Arg Glu Gln Ala Asn Ser
1               5                   10                  15

gaa cgt tgg gat gga gga tca gga ggt acc act tct ccc ttc aaa ctt       96
Glu Arg Trp Asp Gly Gly Ser Gly Gly Thr Thr Ser Pro Phe Lys Leu
            20                  25                  30

cct gac gaa agt ccg agt tgg act gag tgg cgg cta cat aac gat gag      144
Pro Asp Glu Ser Pro Ser Trp Thr Glu Trp Arg Leu His Asn Asp Glu
        35                  40                  45

acg aat tcg aat caa gat aat ccc ctt ggt ttc aag gaa agc tgg ggt      192
Thr Asn Ser Asn Gln Asp Asn Pro Leu Gly Phe Lys Glu Ser Trp Gly
    50                  55                  60

ttc ggg aaa gtt gta ttt aag aga tat ctc aga tac gac agg acg gaa      240
Phe Gly Lys Val Val Phe Lys Arg Tyr Leu Arg Tyr Asp Arg Thr Glu
65                  70                  75                  80

gct tca ctg cac aga gtc ctt gga tct tgg acg gga gat tcg gtt aac      288
Ala Ser Leu His Arg Val Leu Gly Ser Trp Thr Gly Asp Ser Val Asn
                85                  90                  95

tat gca gca tct cga ttt ttc ggt ttc gac cag atc gga tgt acc tat      336
Tyr Ala Ala Ser Arg Phe Phe Gly Phe Asp Gln Ile Gly Cys Thr Tyr
            100                 105                 110
```

-continued

```
agt att cgg ttt cga gga gtt agt atc acc gtt tct gga ggg tcg cga      384
Ser Ile Arg Phe Arg Gly Val Ser Ile Thr Val Ser Gly Gly Ser Arg
        115                 120                 125

act ctt cag cat ctc tgt gag atg gca att cgg tct aag caa gaa ctg      432
Thr Leu Gln His Leu Cys Glu Met Ala Ile Arg Ser Lys Gln Glu Leu
    130                 135                 140

cta cag ctt gcc cca atc gaa gtg gaa agt aat gta tca aga gga tgc      480
Leu Gln Leu Ala Pro Ile Glu Val Glu Ser Asn Val Ser Arg Gly Cys
145                 150                 155                 160

cct gaa ggt act gag acc ttc gaa aaa gaa agc gag taa                  519
Pro Glu Gly Thr Glu Thr Phe Glu Lys Glu Ser Glu
                165                 170


<210> SEQ ID NO 4
<211> LENGTH: 172
<212> TYPE: PRT
<213> ORGANISM: Tomato bushy stunt virus

<400> SEQUENCE: 4

Met Glu Arg Ala Ile Gln Gly Asn Asp Ala Arg Glu Gln Ala Asn Ser
1               5                   10                  15

Glu Arg Trp Asp Gly Gly Ser Gly Gly Thr Thr Ser Pro Phe Lys Leu
            20                  25                  30

Pro Asp Glu Ser Pro Ser Trp Thr Glu Trp Arg Leu His Asn Asp Glu
        35                  40                  45

Thr Asn Ser Asn Gln Asp Asn Pro Leu Gly Phe Lys Glu Ser Trp Gly
    50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
                85                  90                  95

Tyr Ala Ala Ser Arg Phe Phe Gly Phe Asp Gln Ile Gly Cys Thr Tyr
            100                 105                 110

Ser Ile Arg Phe Arg Gly Val Ser Ile Thr Val Ser Gly Gly Ser Arg
        115                 120                 125

Thr Leu Gln His Leu Cys Glu Met Ala Ile Arg Ser Lys Gln Glu Leu
    130                 135                 140

Leu Gln Leu Ala Pro Ile Glu Val Glu Ser Asn Val Ser Arg Gly Cys
145                 150                 155                 160

Pro Glu Gly Thr Glu Thr Phe Glu Lys Glu Ser Glu
                165                 170
```